United States Patent [19]
Guthauser et al.

[11] Patent Number: 5,290,555
[45] Date of Patent: Mar. 1, 1994

[54] COSMETIC COMPOSITIONS WITH STRUCTURAL COLOR

[75] Inventors: Bernadette Guthauser, North Bergen; William J. Radice, North Brunswick, both of N.J.

[73] Assignee: Revlon Consumer Products Corporation, New York, N.Y.

[21] Appl. No.: 955,378

[22] Filed: Oct. 1, 1992

Related U.S. Application Data

[63] Continuation of Ser. No. 756,724, Sep. 9, 1991, abandoned, which is a continuation of Ser. No. 675,390, Apr. 29, 1992, abandoned, which is a continuation of Ser. No. 407,347, Sep. 14, 1989, abandoned.

[51] Int. Cl.$^5$ .............................................. A61K 6/00
[52] U.S. Cl. .................................... 424/401; 424/63; 424/61; 424/70; 424/71
[58] Field of Search .................. 424/63, 70, 78.03, 71, 424/61, 73

[56] References Cited

U.S. PATENT DOCUMENTS

| | | | |
|---|---|---|---|
| 4,883,659 | 11/1989 | Goodman et al. | 424/78.03 |
| 5,034,218 | 7/1991 | Duvel | 424/70 |
| 5,085,854 | 2/1992 | Fukuda et al. | 424/63 |

*Primary Examiner*—Thurman K. Page
*Assistant Examiner*—William E. Benston
*Attorney, Agent, or Firm*—Julie Blackburn

[57] ABSTRACT

Cosmetic compositions which display structural color include at least two cosmetically acceptable liquid phases, either or both of which contain cosmetically efficacious agents, the phases being selected to have the same refractive index, but different dispersive power.

9 Claims, No Drawings

COSMETIC COMPOSITIONS WITH STRUCTURAL COLOR

This is a continuation Ser. No.07/756,724 filed on Sept. 9, 1991 abandoned; which is in turn a continuation of Ser. No. 675,390 filed Apr. 29, 1992 abandoned; which is in turn a continuation of Ser. No. 407,347 filed Sept. 14, 1989 abandoned.

This invention is in the field of body-treating compositions. More particularly, this invention is directed to cosmetic compositions, specifically cosmetic compositions which exhibit the optical phenomenon known as "structural color."

BACKGROUND OF THE INVENTION

From the earliest of times human beings have been concerned with their appearance and the condition of their external features, their skin, hair, fingernails, etc. Accordingly, a myriad of cosmetic compositions have been developed to satisfy the demand for such products. Cosmetics often are designed to have both utilitarian and aesthetic appeal. Although the utilitarian aspects of the compositions of this invention have not been neglected, it is primarily with the aesthetic aspects that this invention is concerned. In this regard, the cosmetic compositions of this invention exhibit a beautiful and intriguing phenomenon known as "structural color."

Briefly, when two transparent, immiscible liquids are mixed, the combination is often cloudy. If, however, the liquids have the same refractive index (generally measured at 589 nm, i.e., the sodium D line, and 20° C., viz., "$n_D^{20}$"), the mixture will be substantially transparent to the human eye and appear to be homogeneous. The appearance of "structural color" in such a mixture requires, not only that the refractive indexes (at a given wavelength of visible light) are the same, but that the variation of the indexes as a function of visible wavelength differ for the two liquids. That is, the "dispersive power" of the two phases must be different.

Chemical systems which exhibit structural color have been referred to as "chromatic emulsions" by Holmes and Cameron, *J. Am. Chem. Soc.*, 44, pp 71-74 (1922), who traced the first report of the phenomenon to 1913. Indeed the liquid mixtures may contain emulsifying agents, and the mixtures may be transparent emulsions. Emulsions are especially useful in cosmetic applications; see, e.g., *Cosmetics & Toiletries*, 101, pp 25-44 (1986). However, emulsification is not a requirement.

Holmes and Cameron provided the following illustrations: When glycerol ($n_D^{20}=1.4660$) and amyl acetate ($n_D^{20}=1.4012$) were shaken together, a milky-white mixture resulted, a typical emulsion. However, when water ($n_D^{20}=1.3330$) was added to the glycerol until $n_D^{20}$ of that solution was 1.4012, and amyl acetate was shaken with the solution, a perfectly transparent emulsion was obtained; however, no color is reported. Further, the authors report: "In attempting to disperse glycerol in an acetone solution of cellulose nitrate we failed to get transparency. Since the index of refraction of the acetone (1.35886) was lower than that of the glycerol (1.4660) we added benzene (1.50144) cautiously to the milky emulsion in order to equalize the indices of the two liquid phases of course the benzene diluted the acetone thus becoming part of the continuous phase. With cautious additions, and shaking, increased transparency was secured but accompanied by a startling development of colors. At first the emulsion became yellow as viewed from the side and a soft blue when held between the eye and the source of light. With further addition of benzene the yellow changed to beautiful pink while the blue became green. More benzene changed the pink to lavender and later to a peacock-blue. Finally, the emulsion lost color and became milky. The colors are restored, in reverse order, by cautious additions of acetone."

Structural color as exhibited in chromatic emulsions has been described subsequent to the paper of Holmes and Cameron. Such reports appear in *J. Phys. Chem.*, 56, pp 510-513 (1952) and in P. Becher, "Emulsions: Theory and Practice," 2nd Ed., Reinhold Publishing Corp., New York, N.Y., 1965, p 58, for example. The systems described in this prior art were not directed toward cosmetic applications, and the need to use cosmetically acceptable components was not addressed; rather, aromatic hydrocarbons (e.g., benzene), halocarbons (e.g., chloroform and carbon tetrachloride), and amines (e.g., pyridine) were mentioned as components.

Transparent emulsions which might have application in cosmetics are disclosed in *Int'L. J. Cosmet. Sci.*, 8, pp 1-8 (1986) and in UK published application 2 079 300 A, for example. Various cosmetically acceptable components are cited, including silicone compounds. However, none of the cosmetic compositions is said to exhibit structural color, so the requirement of a difference in dispersive power between the two phases apparently was neither sought nor achieved.

To be distinguished from the emulsions of this invention, which exhibit structural color, are transparent microemulsions in which the transparency is achieved, not by virtue of refractive index matching, but rather by controlling the diameter of the dispersed phase particles, making them so small, less than about 0.05 micron, that they cannot be resolved by visible light. The compositions of this invention are not restricted to emulsions; but to the extent the compositions are emulsions, they can, if desired, be macroemulsions, no attempt being required to control the dispersed phase particle size.

Consequently, it is one object of this invention to provide useful cosmetic compositions with the aesthetic feature of exhibiting structural color. It is another objective to provide such compositions using cosmetically acceptable components.

SUMMARY OF THE INVENTION

In achieving the aforesaid objectives, this invention provides cosmetic compositions which comprise a mixture of at least two cosmetically acceptable, incompletely miscible fluid phases, generally a continuous phase and a dispersed phase, any or all of the phases including cosmetically effective amounts of cosmetically efficacious components, and the phases exhibiting substantially the same refractive index, but different dispersive power, whereby the compositions display structural color phenomena. Examples of two phase systems include silicone fluids and water. Three phase systems could include a silicone phase, a vegetable oil phase, and water, for example.

The choice of cosmetically efficacious components from the wide range of materials known in the art permits construction of cosmetic compositions within the scope of this invention which have a spectrum of uses. For example, cosmetic compositions exhibiting structural color may include shampoos, hair conditioners, after shave lotions, various skin moisturizers, nail polish removers, skin cleansing products, skin bleaching lotions, skin fresheners, splashes, moisturizing colognes, and suntan lotions.

DETAILED DESCRIPTION

The cosmetically efficacious components can be present in one or more of the phases in a cosmetically effective amount and are selected on the basis of the functional and aesthetic qualities desired in the product, qualities and quantities which are well known in the art for various components. However, the cosmetically efficacious components must also be selected from those which provide substantially translucent, if not substantially transparent, and preferably colorless individual phases in the cosmetic compositions.

One phase may, for example, contain components which are miscible primarily with water and/or alcohol, while the other phase contains components which are primarily miscible with hydrocarbons, vegetable oils, or silicone compounds. In formulating the mixtures which constitute the compositions of this invention into emulsions, either phase generally can be made to be the continuous or the dispersed phase by including an emulsifying agent selected according to hydrophiliclipophilic balance criteria which are well known in the art.

The selection of major components of the cosmetic compositions must be made with an eye toward their optical properties, i.e. color, refractive index and dispersive power. The refractive indexes and the colors of numerous chemical compounds can be found in the various well known handbooks of chemistry. The dispersive power of some common liquids is provided in references cited above. The International Critical Tables provides both refractive index and dispersive power for a number of liquids. However, it should be appreciated that a certain amount of experimentation is often necessary to achieve the delicate balances required in producing the cosmetic compositions of this invention.

A useful technique for screening pairs of incompletely miscible fluid phases for the structural color phenomenon is to combine the two phases with vigorous stirring and titrate the mixture with one of the components to the appearance of color. For example, if aqueous and oil phases are to be combined, one can begin with the refractive index of the aqueous phase adjusted 0.04–0.08 higher than the refractive index of the oil phase, e.g., by adding glycerol. The phases are then mixed, and the mixture is titrated with pure water, which has a relatively low refractive index (1.333), to the point where either turbidity or color is observed. If the mixture becomes turbid or opaque without first passing through a color transition, it must be concluded the difference in dispersive power between the two phases is too small for the mixture to exhibit structural color.

In preferred embodiments, one phase is aqueous or alcoholic and the other phase contains one or more cosmetically acceptable silicone-type polymers. In this regard, dimethicone, phenyl trimethicone and cyclomethicone, including mixtures thereof, are especially useful. In selecting suitable polymers of these types it is desirable that the viscosity of polymer solutions lie in the range of about 0.1 centipoise to about $10^6$ centipoise at 25° C. Emollients such as fatty acid esters, fatty alcohols, and hydrocarbons may also be employed advantageously. The relative amounts of the two phases is not critical; the dispersed phase may constitute between about 10 percent and about 80 percent by weight of the cosmetic composition.

Although the invention includes compositions which are otherwise, in preferred embodiments the compositions include at least one emulsifying agent, and the compositions are emulsions. The emulsifying agent should be substantially transparent and/or soluble in one of the phases and compatible with the other components of the composition. Functionally, the emulsifying agent can be anionic, such as sodium lauryl sulfate, cationic, such as olealkonium chloride, nonionic, such as Polysorbate 20, or amphoteric The backbone of the emulsifier molecule can be aliphatic, aromatic, or a polysiloxane chain; it can be straight-chained or branched and combine any of the aforesaid structural possibilities.

Especially preferred embodiments include cosmetic compositions which are skin moisturizers, suntan lotions, after-shave lotions, shampoos, skin-bleaching lotions, nail polish remover, cleansing gels, hair conditioners, splashes, and hydroalcoholic skin fresheners and coolers.

The invention will be clarified by reference to the following Examples which illustrate its application.

The following cosmetic compositions were prepared by separately mixing the phases, having first determined their refractive indexes (RI) and adjusted them to be nearly the same, and then combining the two with stirring in a colorless glass vessel. The refractive indexes were then matched by adding a component, generally one of those already present, in a quantity sufficient (QS) to achieve structural color in the composition. All quantities in the Examples are in parts by weight unless stated otherwise. Each component in the Examples is named in accordance with the usual chemical name, the "CTFA Adopted Name," as set forth in "CTFA Cosmetic Ingredient Dictionary," Third Ed., The Cosmetic, Toiletry and Fragrance Association, Inc., Washington, D.C., 1982, or trade name.

EXAMPLE 1

Shampoo

|  | Quantity |
|---|---|
| Aqueous Phase Components |  |
| Water | 18.87 |
| QS to color | 2–4 |
| Urea | 18.87 |
| Sodium Laureth Sulfate (25% aq.) | 28.30 |
| PEG-6 Caprylic/Capric Glycerides | 18.87 |
| Oil Phase Components |  |
| Dimethicone (0.65 cts.)[6] | 9.0 |
| Cetyl Dimethicone Copolyol Polyglyceryl-4 Isostearate Hexyl Laurate[1] | 1.5 |
| Phenyl Trimethicone | 6.0 |

The resultant composition was light blue in color.

EXAMPLE 2

Make Up Remover

|  | Quantity |
|---|---|
| Oil Phase Components (RI 1.448) |  |
| Isododecane | 11.5 |
| Sorbitan Sesquioleate | 3.2 |
| Olive Oil | 11.5 |
| Aqueous Phase Components (RI 1.446) |  |
| Water | 11.5 |

-continued

| | Quantity |
|---|---|
| PEG-8 | 57.0 |
| QS to color | 0.5–1.5 |

The resultant composition was faint bluish-yellow in color.

EXAMPLE 3

Moisturizer

| | Quantity |
|---|---|
| Aqueous Phase Components (RI 1.421) | |
| Water | 28.0 |
| QS to color | 3–5 |
| Polysorbate 20 | 2.0 |
| PEG-8 | 42.0 |
| Oil Phase Components (RI 1.411) | |
| Neo pentyl glycol Dicaprylate/Dicaprate | 10.0 |
| Dimethicone (0.65 cts.)[6] | 10.0 |

The resultant composition was bluish-yellow.

EXAMPLE 4

Moisturizer

| | Quantity |
|---|---|
| Aqueous Phase Components | |
| Water | 15.0 |
| QS to color | 1–2 |
| PEG-8 | 45.0 |
| Steareth-20 | 4.0 |
| Oil Phase Components | |
| Olive Oil | 18.0 |
| Isododecane | 18.0 |

The color of the resultant composition was yellowish-blue.

EXAMPLE 5

After Shave Lotion

| | Quantity |
|---|---|
| Aqueous Phase Components | |
| SD Alcohol 40 | 20.0 |
| QS to color | 4.4 |
| PEG-8 | 13.0 |
| Butylene Glycol | 10.0 |
| Water | 5.0 |
| Urea | 5.0 |
| Polyvinylpyrrolidone | 0.12 |
| Oil Phase Components | |
| Phenyl Trimethicone | 7.0 |
| Cyclomethicone | 30.0 |
| Cetyl Dimethicone Copolyol Polyglyceryl-4 Isostearate Hexyl Laurate[1] | 5.0 |
| Nonoxynol-2 | 2.0 |
| Fragrance | 1.0 |

The color of the composition was slightly translucent yellow/light blue.

EXAMPLE 6

Sun Protection Lotion

| | Quantity |
|---|---|
| Oil Phase Components (RI 1.4395) | |
| $C_9$–$C_{10}$ Isoparaffin | 30.0 |
| Propylene Glycol Dicaprylate/Dicaprate | 20.0 |
| Octyl methoxycinnamate | 5.0 |
| Oleic Acid | 3.0 |
| Polysorbate 80 | 3.0 |
| Aqueous Phase Components (RI 1.444) | |
| Potassium Hydroxide, 10% aq. | 2.0 |
| Water | 6.0 |
| QS to color | 4.0 |
| Butylene Glycol | 2.0 |
| PEG-8 | 30.0 |

The color of the composition was yellow/white/light blue.

EXAMPLE 7

Moisturizer

| | Quantity |
|---|---|
| Aqueous Phase Components (RI 1.418) | |
| Methylparaben | 0.25 |
| Propylene Glycol | 3.2 |
| Butylene Glycol | 2.0 |
| Water | 20.0 |
| QS to color | 11.2 |
| Laureth-23 | 2.0 |
| Urea | 3.0 |
| PEG-8 | 26.55 |
| Oil Phase Components (RI 1.405) | |
| Cyclomethicone | 32.0 |
| Cetyl Dimethicone Copolyol Polyglyceryl-4 Isostearate Hexyl Laurate[1] | 5.0 |
| Cetyl Dimethicone Copolyol[2] | 1.0 |
| Tocopheryl Acetate | 0.1 |

The color of the composition was hazy blue/white.

EXAMPLE 8

Moisturizer

| | Quantity |
|---|---|
| Aqueous Phase Components (RI 1.4375) | |
| Propylene Glycol | 3.75 |
| Methylparaben | 0.25 |
| Urea | 3.0 |
| Imidazolidinyl Urea | 0.3 |
| Water | 15.0 |
| QS to color | 8.6 |
| PEG-8 | 31.0 |
| Butylene Glycol | 2.0 |
| Laureth 23 | 2.0 |
| Oil Phase Components (RI 1.423) | |
| Cyclomethicone | 20.0 |
| Cetyl Dimethicone Copolyol Polyglyceryl-4 Isostearate Hexyl Laurate[1] | 5.0 |
| Phenyl Trimethicone | 6.0 |
| Cetearyl Octanoate | 6.0 |
| Tocopheryl Acetate | 0.1 |
| Cetyl Dimethicone Copolyol[2] | 1.0 |

The color of the composition was hazy blue/white.

EXAMPLE 9

Moisturizer

| | Quantity |
|---|---|
| Aqueous Phase Components | |
| Propylene Glycol | 3.3 |
| Preservatives[3] | 0.4 |
| Urea | 2.0 |
| Water | 18.4 |
| QS to color | 1.0 |
| PEG-8 | 27.0 |
| PEG-120 Methyl Glucose Dioleate | 5.0 |
| Oil Phase Components | |
| Cetyl Dimethicone Copolyol Polyglyceryl-4 Isostearate Hexyl Laurate[1] | 5.0 |
| Isopropyl Stearate | 15.0 |
| Cyclomethicone | 15.0 |
| Octyl Dimethyl PABA | 2.0 |
| Trioleyl Phosphate | 2.0 |
| Cyclomethicone (and) Dimethicone Copolyol[4] | 5.0 |

The color of the composition was soft green/purple.

EXAMPLE 10

Nail Polish Remover

| | Quantity |
|---|---|
| Oil Phase Components (RI 1.398) | |
| Ethyl Acetate | 14.6 |
| Acetone | 14.6 |
| Cetyl Dimethicone Copolyol Polyglyceryl-4 Isostearate Hexyl Laurate[1] | 5.0 |
| Cetyl Dimethicone Copolyol[2] | 2.0 |
| Cyclomethicone | 6.0 |
| Aqueous Phase Components (RI 1.457) | |
| Isopropyl alcohol | 10.8 |
| Water | 4.0 |
| QS to color | 6.2 |
| PEG-8 | 40.0 |
| Talloweth-60 Myristyl Glycol | 2.0 |

The color of the composition was translucent/blue.

EXAMPLE 11

Cleansing Gel

| | Quantity |
|---|---|
| Continuous Phase Components | |
| Cetyl Dimethicone Copolyol Polyglyceryl-4 Isostearate Hexyl Laurate[1] | 3.0 |
| Phenyl Trimethicone | 15.0 |
| Fumed Silica, 6% in Mineral Oil | 33.0 |
| Cyclomethicone    QS to color | 1.0 |
| Dispersed Phase Components | |
| Methylparaben | 0.35 |
| Propylene Glycol | 5.1 |
| PEG-8 | 42.55 |
| PPG-20 Methyl Glucose Ether | 1.0 |

The color of the composition was transparent yellow.

EXAMPLE 12

Cleansing Gel

| | Quantity |
|---|---|
| Continuous Phase Components | |
| Cetyl Dimethicone Copolyol Polyglyceryl-4 Isostearate Hexyl Laurate[1] | 3.0 |
| Phenyl Trimethicone | 15.0 |
| Fumed Silica, 6% in Mineral Oil | 28.0 |
| Methyl Anthranilate | 0.2 |
| Dispersed Phase Components | |
| Methylparaben | 0.35 |
| Propylene Glycol | 5.1 |
| PEG-8 | 42.55 |
| PPG-10 Methyl Glucose Ether | 1.0 |
| Hydroxypropylcellulose, 4% in PEG-8 | 5.0 |
| QS to color | 2.0 |

The color of the composition was transparent blue.

EXAMPLE 13

Hair Conditioner

| | Quantity |
|---|---|
| Oil Phase Components (RI 1.423) | |
| Polysiloxane Polydimethyl Dialkyammonium Acetate Copolymer[5] | 10.0 |
| Cetyl Dimethicone Copolyol[2] | 2.0 |
| Phenyl Trimethicone | 8.0 |
| Cyclomethicone | 8.0 |
| Aqueous Phase Components (RI 1.4425) | |
| Water | 10.0 |
| QS to color | 5.4 |
| Olealkonium Chloride (50% aq.) | 3.0 |
| PEG-8 | 40.0 |

The color of the composition was yellow/blue.

EXAMPLE 14

Skin Bleaching Lotion

| | Quantity |
|---|---|
| Oil Phase Components (RI 1.4325) | |
| Cyclomethicone | 20.0 |
| Octyl Methoxycinnamate | 2.0 |
| Cetyl Dimethicone Copolyol Polyglyceryl-4 Isostearate Hexyl Laurate[1] | 5.0 |
| Phenyl Trimethicone | 6.0 |
| Cetearyl Octanoate | 6.0 |
| Tocopheryl Acetate | 0.1 |
| Cetyl Dimethicone Copolyol[2] | 1.0 |
| Fragrance | 3.0 |
| Aqueous Phase Components (RI 1.438) | |
| Methylparaben | 0.25 |
| Butylene Glycol | 2.0 |
| Propylene Glycol | 3.3 |
| Urea | 3.0 |
| Water | 12.6 |
| QS to color | 2.7 |
| Laureth-23 | 1.0 |
| Imidazolidinyl Urea | 0.3 |
| Hydroquinone | 2.0 |
| Sodium Bisulfite | 0.4 |
| PEG-8 | 27.45 |

The color of the composition was yellow/blue.

EXAMPLE 15

Suntan Lotion

| | Quantity |
|---|---|
| Oil Phase Components | |
| Isopropyl Stearate | 10.0 |
| Cyclomethicone | 20.0 |
| Methyl Anthranilate | 3.5 |
| Octyl Methoxycinnamate | 3.0 |
| Oleamide Diethanolamine | 3.0 |

-continued

| | Quantity |
|---|---|
| Cyclomethicone (and) Dimethicone Copolyol[4] | 10.0 |
| Fragrance | 0.1 |
| Aqueous Phase Components | |
| Propylene Glycol | 2.8 |
| Preservatives[3] | 0.4 |
| Urea | 6.0 |
| Water | 8.4 |
| QS to color | 6.2 |
| Sodium Diethylsulfosuccinate (75% aq.) | 3.0 |
| PEG-8 | 23.7 |

When viewed from the side, the composition was sparkling yellow, with patches and longitudinal striations of a light blue; but viewed when held up between the eyes and the light source, the blue of a singular purity dominated over the yellow.

EXAMPLE 16

Suntan Lotion

| | Quantity |
|---|---|
| Oil Phase Components | |
| Isopropyl Stearate | 10.0 |
| Cyclomethicone | 17.0 |
| Methyl Anthranilate | 3.5 |
| Octyl Methoxycinnamate | 3.0 |
| Cyclomethicone (and) Dimethicone Copolyol[4] | 7.0 |
| Fragrance | 0.1 |
| Isostearic Acid | 4.0 |
| Phenyl Trimethicone | 2.0 |
| Poloxamer 401 | 2.0 |
| Aqueous Phase Components | |
| Propylene Glycol | 2.8 |
| Preservatives[3] | 0.4 |
| F.D. + C RED #4 Dye (0.05% aq.) | 0.07 |
| Water | 16.73 |
| QS to color | 5.7 |
| 2-Amino-2-methyl-1-propanol | 1.1 |
| Sodium Diethylsulfosuccinate (75% aq) | 1.0 |
| PEG-8 | 23.7 |

[1]Available as ABIL WE-09 from Goldschmidt Chemical Company, Hopewell, VA 23860.
[2]Available as ABIL B 9806 from Goldschmidt Chemical Co.
[3]Methyl Paraben 0.25
Trisodium EDTA 0.05
Quaternium-15 0.1
[4]Available as Q2-3225C from Dow Corning Corporation, Midland, MI 48640.
[5]Available as ABIL B 9905 from Goldschmidt Chemical Co.
[6]Available as DC 200 Fluid from Dow Corning, Midland, MI.

The individual phases were clear and substantially colorless, except for the very small amount of red dye added, giving upon shaking a warm reddish/yellow sunset color combination, thus helping to visualize the functional properties of the product.

Having described this invention with reference to a number of cosmetic compositions with a range of utilities, it will be evident the invention is capable of broad application to a wide range of different cosmetic products. The scope of the invention not limited to the specific embodiments described herein, but is set forth in the following claims.

What is claimed is:

1. A cosmetic composition exhibiting structural color, comprising a mixture of at least two immiscible substantially translucent colorless fluid phases having essentially the same refractive index and substantially different dispersive power, Phase A and phase B, wherein phase A is comprised of water, alcohol, or mixtures thereof; and phase B is an oil phase comprising an ingredient selected from the group consisting of vegetable oil, a fatty alcohol, a fatty acid ester, a silicone polymer of viscosity $0.1-10^9$ centipoise at 25° C., or mixtures thereof; wherein one phase is dispersed into the other phase and the dispersed phase is 10-80% of the composition.

2. The composition of claim 1 wherein Phase B comprises a silicone polymer of viscosity $0.1-10^6$ centipoise at 25° C.

3. The composition of claim 2 additionally comprising an emulsifying agent.

4. The composition of claim 3 wherein the emulsifying agent is is selected from the group consisting of an anionic, cationic, nonionic, and amphoteric surfactant.

5. The composition of claim 4 wherein the emulsifying agent is selected from the group consisting of sodium laureth sulfate, cetyl dimethicone copolyol polyglyceryl-4-isostearate hexyl laurate, sorbitan sesquioleate, steareth-20, nonoxynol-2, talloweth60 myristyl glycol, cetyl dimethicone copolyol, polysiloxane polydimethyl dialkylammonium acetate copolymer, Polysorbate 20, Polysorbate 80, or mixtures thereof.

6. The composition of claim 5 wherein the silicone is selected from the group consisting of dimethicone, phenyl trimethicone, cyclomethicone, or mixtures thereof.

7. The composition of claim 1 wherein Phase B comprises vegetable oil.

8. The composition of claim 1 further comprising a colored dye.

9. A method for the manufacture of a cosmetic composition exhibiting structural color, from two incompletely miscible, substantially translucent colorless fluid phases exhibiting essentially the same refractive index but substantially different dispersie power, Phase A and Phase B, wherein Phase A comprises water, alcohol, or mixtures thereof; and Phase B is an oil phase containing an ingredient selected from the group consisting of vegetable oil, a fatty alcohol, a fatty acid ester, a silicone polymer of viscosity $0.1-10^6$ cps at 25° C., or mixtures thereof; comprising the steps of:

a) adjusting Phase A and Phase B to nearly the same refractive index,
b) combining Phases A and B,
c) adding to this mixture an additional amount of an ingredient already present in Phase A or Phase B until structural color is achieved.

* * * * *

UNITED STATES PATENT AND TRADEMARK OFFICE
CERTIFICATE OF CORRECTION

PATENT NO. : 5,290,555

DATED : March 1, 1994

INVENTOR(S) : Guthauser, et al.

It is certified that error appears in the above-identified patent and that said Letters Patent is hereby corrected as shown below:

Title page,
item [63], under the heading "Related U.S. Application Data", after [63] the paragraph should read:

Continuation of Ser.No. 756,724, Sep. 9, 1991, abandoned, which is a continuation of Ser.No. 675,390, Apr. 29, 1991, abandoned, which is a continuation of Ser.No. 407,347, Sep. 14, 1989, abandoned.

After "which is a continuation of Ser. No. 675,390, Apr. 29", the "1992" was deleted and "1991" inserted.

Signed and Sealed this

Third Day of January, 1995

*Attest:*

BRUCE LEHMAN

*Attesting Officer*     *Commissioner of Patents and Trademarks*